United States Patent
Imahashi

(10) Patent No.: US 9,517,052 B2
(45) Date of Patent: Dec. 13, 2016

(54) ULTRASOUND ENDOSCOPE

(71) Applicant: OLYMPUS CORPORATION, Tokyo (JP)

(72) Inventor: Takuya Imahashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/931,113

(22) Filed: Nov. 3, 2015

(65) Prior Publication Data
US 2016/0051222 A1    Feb. 25, 2016

Related U.S. Application Data

(63) Continuation of application No. PCT/JP2014/077818, filed on Oct. 20, 2014.

(30) Foreign Application Priority Data

Jan. 6, 2014  (JP) ................. 2014-000467

(51) Int. Cl.
A61B 8/00 (2006.01)
A61B 8/12 (2006.01)
A61B 1/00 (2006.01)

(52) U.S. Cl.
CPC ............... *A61B 8/445* (2013.01); *A61B 8/12* (2013.01); *A61B 8/4281* (2013.01); *A61B 8/4455* (2013.01); *A61B 8/4494* (2013.01); *A61B 1/00101* (2013.01)

(58) Field of Classification Search
CPC ..... A61B 1/00101; A61B 8/12; A61B 8/4281; A61B 8/445; A61B 8/4455; A61B 8/4494
See application file for complete search history.

(56) References Cited

U.S. PATENT DOCUMENTS 5,176,140 A * 1/1993 Kami .................. A61B 8/12
310/327
2013/0072801 A1   3/2013  Hiraoka
2013/0158410 A1   6/2013  Ohgishi et al.

FOREIGN PATENT DOCUMENTS

EP         2591731 A1   5/2013
EP         2641542 A1   9/2013
JP         S61-73639 A  4/1986
(Continued)

OTHER PUBLICATIONS

International Search Report dated Nov. 25, 2014 issued in PCT/JP2014/077818.

*Primary Examiner* — Michael Rozanski
(74) *Attorney, Agent, or Firm* — Scully, Scott, Murphy & Presser, P.C.

(57) ABSTRACT

An ultrasound endoscope according to the invention includes: an ultrasound transducer that transmits/receives ultrasound; a housing in which the ultrasound transducer is fixed via an adhesive, and which houses the ultrasound transducer; an inner peripheral face forming a rectangular first opening portion for exposing the ultrasound transducer, the first opening portion being formed in the housing; an acoustic lens forming a part from an upper face to at least a side face of the ultrasound transducer; and a chamfered portion provided at a side face of the acoustic lens, an adhesive outlet port for the adhesive to flow to an outside from the first opening portion being formed between the chamfered portion and the inner peripheral face.

5 Claims, 6 Drawing Sheets

(56) References Cited

FOREIGN PATENT DOCUMENTS

| | | |
|---|---|---|
| JP | H09-075345 A | 3/1997 |
| JP | 5185476 B2 | 4/2013 |
| JP | 5253691 B1 | 7/2013 |
| WO | WO 2012/157354 A1 | 11/2012 |
| WO | WO 2013/035374 A1 | 3/2013 |

\* cited by examiner

ULTRASOUND ENDOSCOPE

CROSS REFERENCE TO RELATED APPLICATION

This application is a continuation application of PCT/JP2014/077818 filed on Oct. 20, 2014 and claims benefit of Japanese Application No. 2014-000467 filed in Japan on Jan. 6, 2014, the entire contents of which are incorporated herein by this reference.

BACKGROUND OF THE INVENTION

1. Field of the Invention

The present invention relates to an ultrasound endoscope with an adhesive charged in a housing that houses an ultrasound transducer section.

2. Description of the Related Art

Endoscopes used in a medical field include those that include an insertion portion that can be introduced to a subject, an ultrasound transducer section for transmitting/receiving ultrasound being included in a distal end portion of the insertion portion. For example, Japanese Patent Application Laid-Open Publication No. 9-75345 discloses an ultrasound endoscope including an ultrasound transducer section that can provide ultrasound beam scanning.

An upper face of the ultrasound transducer section, from which ultrasound is transmitted/received, is covered by an acoustic lens. The ultrasound transducer section including the acoustic lens is housed a housing, which is a casing, except the upper face from which ultrasound is transmitted/received. With the ultrasound transducer section including the acoustic lens housed in the housing, an adhesive is charged inside the housing, preventing entry of liquid and/or gas into the housing.

SUMMARY OF THE INVENTION

An ultrasound endoscope according to an aspect of the present invention includes: an ultrasound transducer that transmits/receives ultrasound; a housing in which the ultrasound transducer is fixed via an adhesive, and which houses the ultrasound transducer; an inner peripheral face forming a rectangular first opening portion for exposing the ultrasound transducer, the first opening portion being formed in the housing; an acoustic lens forming a part from an upper face to at least a side face of the ultrasound transducer; and a chamfered portion provided at a side face of the acoustic lens, an adhesive outlet port for the adhesive to flow to an outside from the first opening portion being formed between the chamfered portion and the inner peripheral face.

DETAILED DESCRIPTION OF THE PREFERRED EMBODIMENTS

Figure 1:
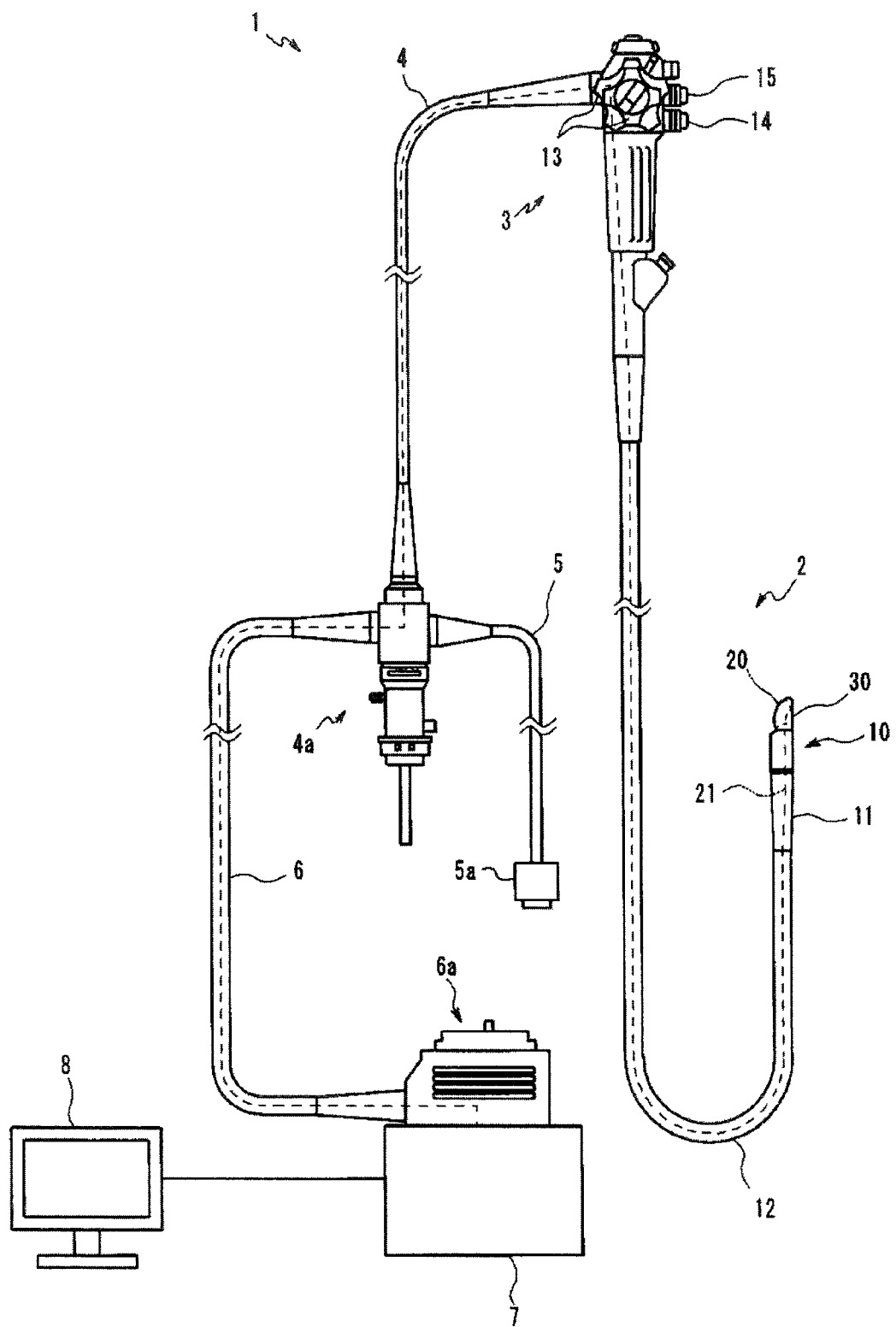
FIG. 1 is a diagram illustrating a configuration of an ultrasound endoscope.

A preferable embodiment of the present invention will be described below with reference to the drawings. Note that in each of the drawings used for the below description, components are illustrated on difference scales so that the respective components have sizes that are large enough to be recognized in the drawing, and the present invention is not limited only to the counts and amounts, and the shapes of the components, and the size ratios and the relative positional relationships among the components illustrated in the drawings.

An ultrasound endoscope 1 according to the present embodiment, which is illustrated in FIG. 1, is an apparatus that obtains an ultrasound tomographic image (B-mode image) of a predetermined part inside a subject by electronically scanning the inside of the subject using an ultrasound beam.

Since an overall configuration of the ultrasound endoscope 1 is publicly known, detailed description thereof will be omitted and a schematic configuration of the ultrasound endoscope 1 will be described below. The ultrasound endoscope 1 mainly includes an insertion portion 2 that can be introduced into the inside of a subject, an operation portion 3 positioned at a proximal end of the insertion portion 2, and a universal cord 4 extending from a side portion of the operation portion 3.

The insertion portion 2 includes a distal end portion 10 disposed at a distal end, a bending portion 11 that is bendable and is disposed on the proximal end side of the distal end portion 10, and a flexible tube portion 12 that has flexibility and is disposed on the proximal end side of the bending portion 11 and connected to the distal end side of the operation portion 3, which are provided consecutively. Note that the ultrasound endoscope 1 may be of what is called a "rigid endoscope" type in which no flexible part is included in the insertion portion 2.

In the distal end portion 10 of the insertion portion 2, in addition to an ultrasound transducer section 20 that transmits/receives ultrasound, which will be described later, although not illustrated, e.g., an image pickup apparatus and an illumination apparatus for picking up an optical image, and a treatment instrument insertion port for letting a treatment instrument project therefrom are provided.

At the operation portion 3, angle operation knobs 13 for operating bending of the bending portion 11 are provided. Also, at the operation portion 3, e.g., switches for controlling operation of liquid feeding and/or operation of liquid suction from opening portions provided in the distal end portion 10 are provided.

At a proximal end portion of the universal cord 4, an endoscope connector 4a connected to a non-illustrated light source apparatus is provided. Light emitted from the light source apparatus passes through an optical fiber cable inserted through the universal cord 4, the operation portion 3 and the insertion portion 2 and is outputted from the illumination apparatus in the distal end portion 10. Note that the ultrasound endoscope 1 may be configured in such a manner that a light source apparatus such as an LED is provided in the illumination apparatus disposed in the distal end portion 10.

An electric cable 5 and an ultrasound cable 6 extend from the endoscope connector 4a. The electric cable 5 is detachably connected to a non-illustrated camera control unit via an electric connector 5a. The camera control unit is an apparatus that outputs an image picked up by the image pickup apparatus provided in the distal end portion 10, to an image display apparatus 8.

Also, the ultrasound cable 6 is detachably connected to an ultrasound observation control apparatus 7 via an ultrasound connector 6a. The ultrasound connector 6a is electrically connected to a plurality of transducer elements 22, which will be described later, included in the ultrasound transducer section 20 via the ultrasound cable 6, the universal cord 4 and a cable 21 inserted through the operation portion 3 and the insertion portion 2.

The ultrasound observation control apparatus 7 is an apparatus that controls ultrasound transmission/reception operation performed by the ultrasound transducer section 20, generates an ultrasound tomographic image and outputs the ultrasound tomographic image to the image display apparatus 8. Note that the ultrasound endoscope 1 may include neither the ultrasound observation control apparatus 7 nor the image display apparatus 8.

Next, a configuration of a part of the ultrasound endoscope 1 in which the ultrasound transducer section 20 is disposed will be described. The ultrasound transducer section 20 is held by a housing 30 in the distal end portion 10 of the insertion portion 3.

Figure 2:
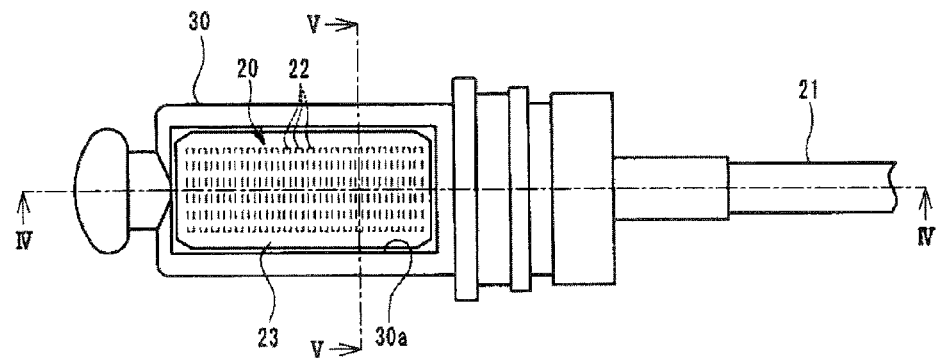
FIG. 2 is a diagram illustrating an upper face of a housing that houses an ultrasound transducer section and an acoustic lens.
Figure 3:
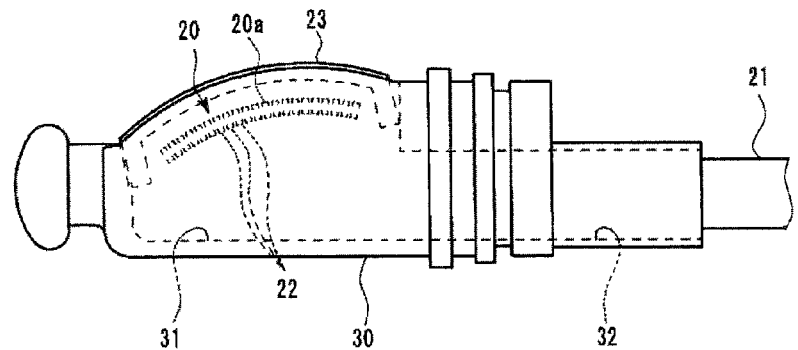
FIG. 3 is a diagram illustrating a side face of the housing that houses the ultrasound transducer section and the acoustic lens.
Figure 4:
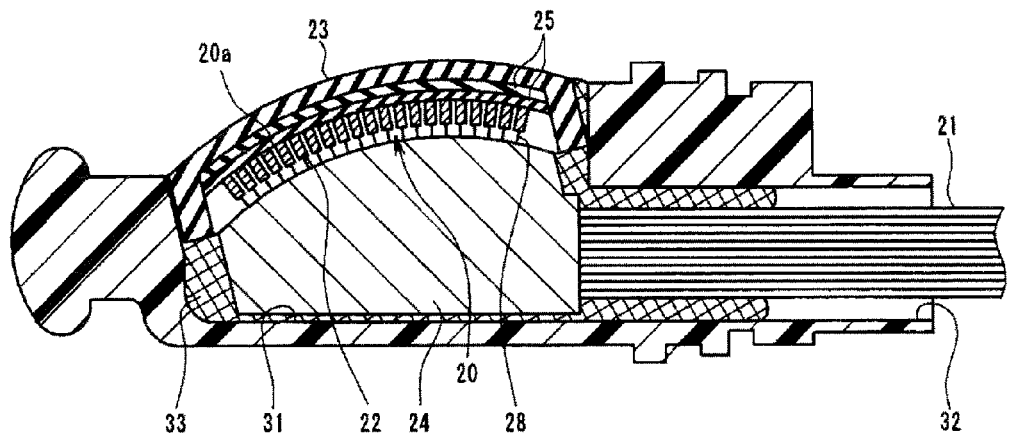
FIG. 4 is a cross-sectional view along IV-IV in FIG. 2.
Figure 5:
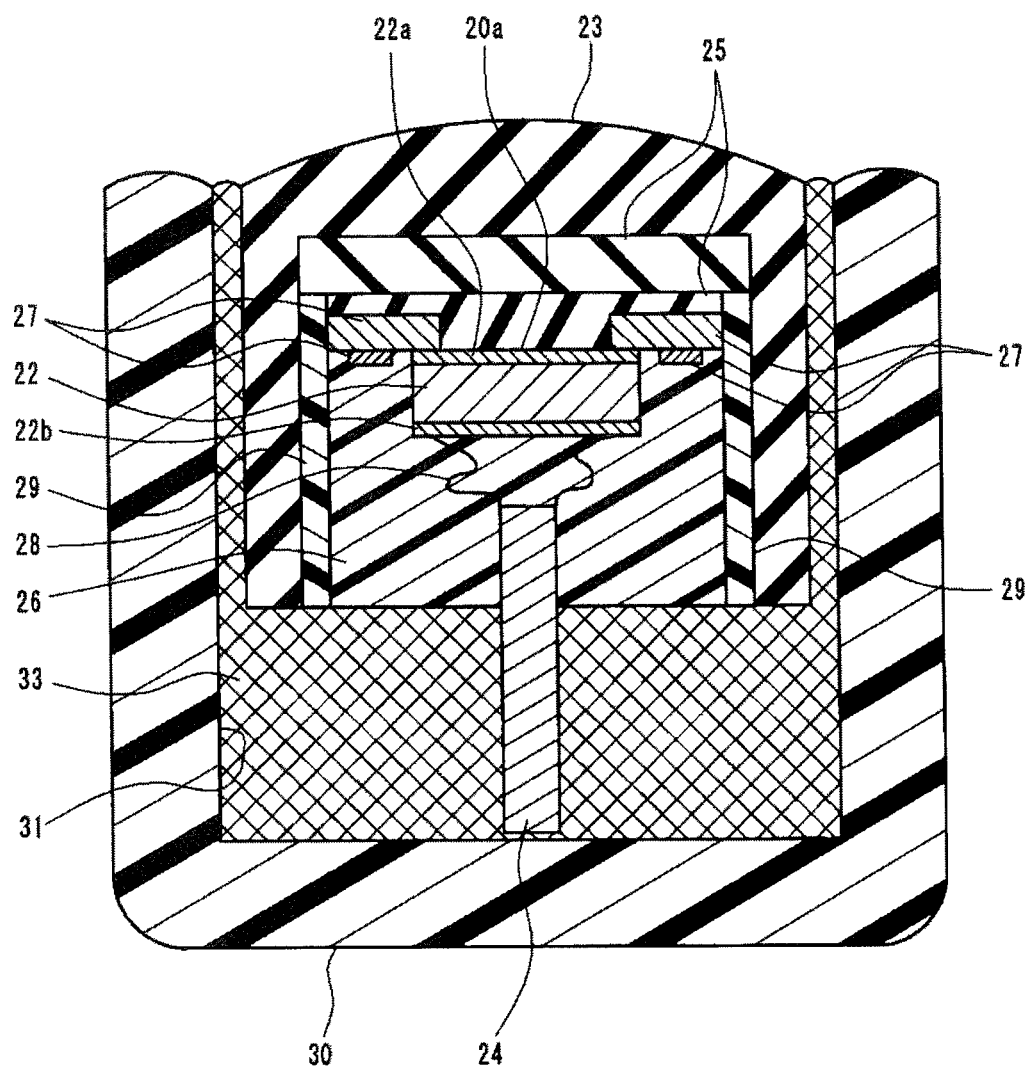
FIG. 5 is a cross-sectional view along V-V in FIG. 2.

FIG. 2 is a diagram illustrating respective upper faces of the ultrasound transducer section 20 and the housing 30. FIG. 3 is a diagram illustrating a side face of the housing 30. FIG. 4 is a cross-sectional view along IV-IV in FIG. 2. FIG. 5 is a cross-sectional view along V-V in FIG. 2.

The ultrasound transducer section 20 includes a plurality of transducer elements 22 aligned in a row. Here, a surface of the ultrasound transducer section 20 from which ultrasound is transmitted/received is referred to as "upper face 20a", and a surface on the opposite side of the upper face 20a is referred to as "lower face". Also, each of faces that intersect with the upper face 20a and the lower face is referred to as "side face". Note that the transducer elements 22 may be aligned in a plurality of rows.

The transducer elements 22 are piezoelectric elements or electrostrictive elements that perform mutual conversion between electric signals and ultrasound or micromachined ultrasonic transducers (MUT).

In the present embodiment, as an example, the transducer elements 22 are piezoelectric elements including a piezoelectric material, and as illustrated in FIG. 5, each include an upper electrode 22a and a lower electrode 22b disposed with the piezoelectric material therebetween. The upper electrode 22a is disposed on the upper face 20a side of the ultrasound transducer section 20, and the lower electrode 22b is disposed on the lower face side.

In response to a voltage applied between the upper electrode 22a and the lower electrode 22b, each transducer element 22 deforms so as to expand/contract in a direction between the upper electrode 22a and the lower electrode 22b. A surface of the lower electrode 22b on the opposite side of the piezoelectric element is in contact with a backing material 26 including a non-conductive material. The backing material 26 is a synthetic resin charged in a holding frame 29 surrounding side faces of the ultrasound transducer section 20 and then cured.

The backing material 26 is a member that absorbs ultrasound radiated from the lower electrode 22b side of the transducer element 22 and ultrasound traveling from the inside of the distal end portion 10 toward the transducer element 22. Thus, in the present embodiment, transmission/reception of ultrasound by each transducer element 22 is performed on the upper face 20a side on which the upper electrode 22a is provided.

In the present embodiment, as an example, the upper face 20a of the ultrasound transducer section 20 is bent in a convex cylindrical face shape projecting outward (upward). The plurality of transducer elements 22 included in the ultrasound transducer section 20 are aligned in a row along a circumferential direction of the upper face 20a.

The upper face 20a of the ultrasound transducer section 20 has a rectangular shape as viewed in a direction along a normal to the upper face 20a. As illustrated in FIG. 2, "as viewed in a direction along a normal to the upper face 20a" refers to a case where the upper face 20a is viewed in a direction facing the upper face 20a of the ultrasound transducer section 20. The plurality of transducer elements 22 are aligned in a row along a longitudinal direction of the upper face 20a of the ultrasound transducer section 20, which has a rectangular shape.

In the present embodiment, the upper face 20a of the ultrasound transducer section 20 has a rectangular shape that bends along a cylindrical face, a longitudinal direction of the rectangular shape being a circumferential direction of the cylindrical face. The ultrasound transducer section 20 can transmit an ultrasound beam in a direction along a normal to the cylindrical face (radial direction), and can provide ultrasound beam scanning in the circumferential direction. The ultrasound endoscope 1 including such ultrasound transducer section 20 as above is generally referred to as an electronic-scanning convex ultrasound endoscope. Note that the type of ultrasound beam scanning by the ultrasound transducer section 20 is not limited to that in the present embodiment, and may be a linear type in which the upper face 20a is a flat shape and the plurality of transducer elements 22 are aligned linearly.

In the present embodiment, the upper electrode 22a of each transducer element 22 is a ground electrode having a ground potential, and the lower electrode 22b is a signal electrode for input/output of a voltage signal. As illustrated in FIG. 5, the upper electrode 22a is electrically connected to the cable 21 via ground potential wirings 27. Also, the lower electrode 22b is electrically connected to the cable 21 via signal wirings 28 and a circuit board 24. The circuit board 24 and the transducer element 22 are fixed by the backing material 26.

On the upper face 20a of the ultrasound transducer section 20, an acoustic matching layer 25 is disposed. The acoustic matching layer 25 is a member that performs acoustic impedance matching between the transducer elements 22 and a later-described acoustic lens 23. The acoustic matching layer 25 is provided as appropriate according to a difference in acoustic impedance between the transducer elements 22 and the acoustic lens 23. Therefore, for example, the acoustic matching layer 25 is not necessary if the difference in acoustic impedance between the transducer elements 22 and the acoustic lens 23 is small. Also, the acoustic matching layer 25 may have a form in which a plurality of layers including different materials are stacked in a thickness direction, or a form of a single layer.

Figure 6:
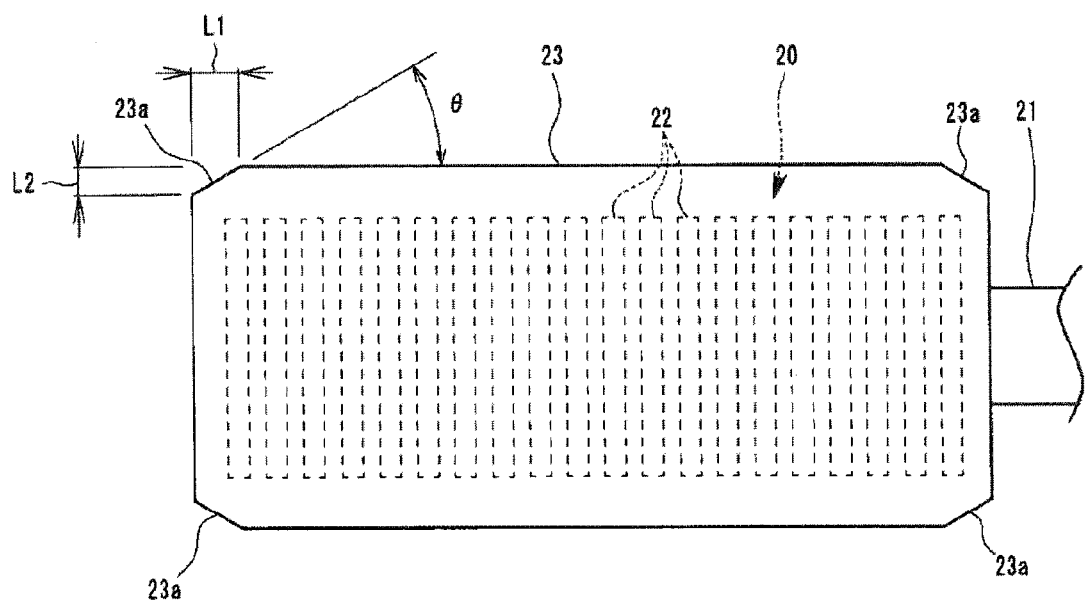
FIG. 6 is a diagram illustrating respective upper faces of the ultrasound transducer section and the acoustic lens.
Figure 7:
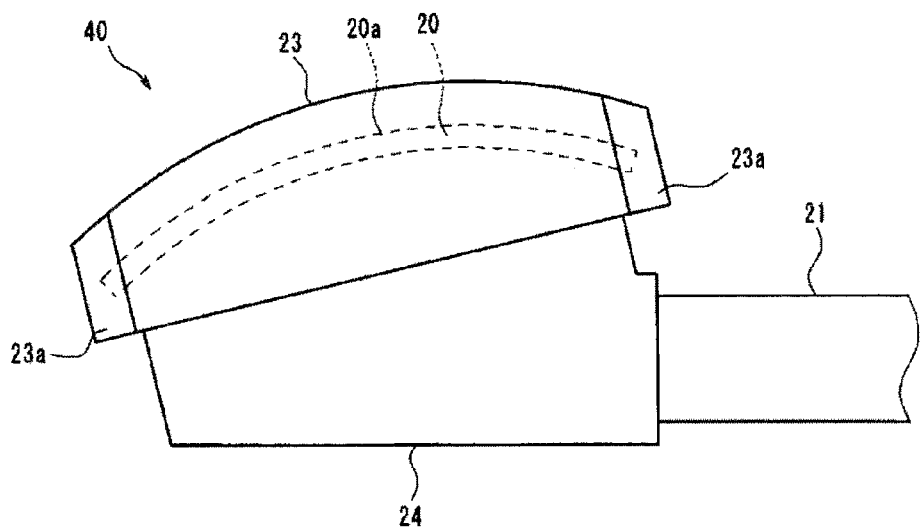
FIG. 7 is a diagram illustrating respective side faces of the ultrasound transducer section and the acoustic lens.

The acoustic lens 23 is a member covering the upper face 20a and the side faces of the ultrasound transducer section 20. The acoustic lens 23 includes a non-conductive material such as silicone, for example. FIG. 6 is a view of respective upper faces of the ultrasound transducer section 20 and the acoustic lens 23 covering the ultrasound transducer section 20. FIG. 7 is a view of respective side faces of the ultrasound transducer section 20 and the acoustic lens 23 covering the ultrasound transducer section 20.

As illustrated in FIG. 6, the acoustic lens 23 covers the upper face 20a and the side faces of the ultrasound transducer section 20, thereby forming a quadrangular prism shape. More specifically, as viewed in a direction facing the upper face 20a, an outer shape of the acoustic lens 23 is a rectangular shape whose longitudinal direction is a direction in which the transducer elements 22 are aligned.

Then, in at least one corner from among four corners of the outer shape of the acoustic lens 23 as viewed from the direction facing the upper face 20a, a chamfered portion 23a resulting from the corner being cut off is formed. The chamfered portion 23a is formed over an entire edge line of the corner of the acoustic lens 23. In the present embodiment, as an example, the chamfered portion 23a is formed at each of the four corners of the outer shape of the acoustic lens 23.

More specifically, as illustrated in FIG. 6, an angle θ of each chamfered portion 23a relative to a long side of the upper face of the acoustic lens 23 having a rectangular shape as viewed in the direction facing the upper face 20a is less than 45 degrees. In other words, the angle θ of each chamfered portion 23a relative to a side of the upper face of the acoustic lens 23 that is parallel to the direction in which the transducer elements 22 are aligned is less than 45 degrees.

In other words, when viewed from a direction facing the upper face 20a, a shape of a part of the upper face 20a that has been cut off as a result of the corresponding chamfered portion 23a of the acoustic lens 23 being formed is a right triangular shape whose side parallel to the direction in which the transducer elements 22 are aligned has a length L1 that is longer than a length L2 of a side perpendicular to the side having the length L1.

As described above, each part of the right triangular shape that has been cut off as a result of the corresponding chamfered portion 23a being formed is made to have a shape elongated in the direction in which the transducer elements 22 are aligned, enabling decrease in ratio of the chamfered portion 23a relative to the length of the short side of the upper face 20a as viewed in the direction facing the upper face 20a. Consequently, interference between the chamfered portions 23a and the transducer elements 22 can be avoided, enabling prevention of increase in length of the short sides of the acoustic lens 23 due to the provision of the chamfered portions 23a.

In assembly of the ultrasound endoscope 1, as illustrated in FIGS. 6 and 7, an ultrasound unit 40 formed by connecting the ultrasound transducer section 20 to a distal end of the cable 21 and fixing the acoustic lens 23 to the ultrasound transducer section 20 is fabricated. Then, the ultrasound unit 40 is housed and secured in the later-described housing 30.

The housing 30 is a casing including a space for housing the ultrasound unit 40 inside. In the housing 30, a first opening portion 31 via which the upper face of the acoustic lens 23 that transmits ultrasound from the ultrasound transducer section 20 is exposed to the outside, and a second opening portion 32 via which the cable 21 is connected to the ultrasound transducer section 20 is drawn out are formed. The acoustic lens 23 and the ultrasound transducer section 20 housed in the housing 30 are secured by an adhesive 33 charged in the housing 30.

Figure 8:
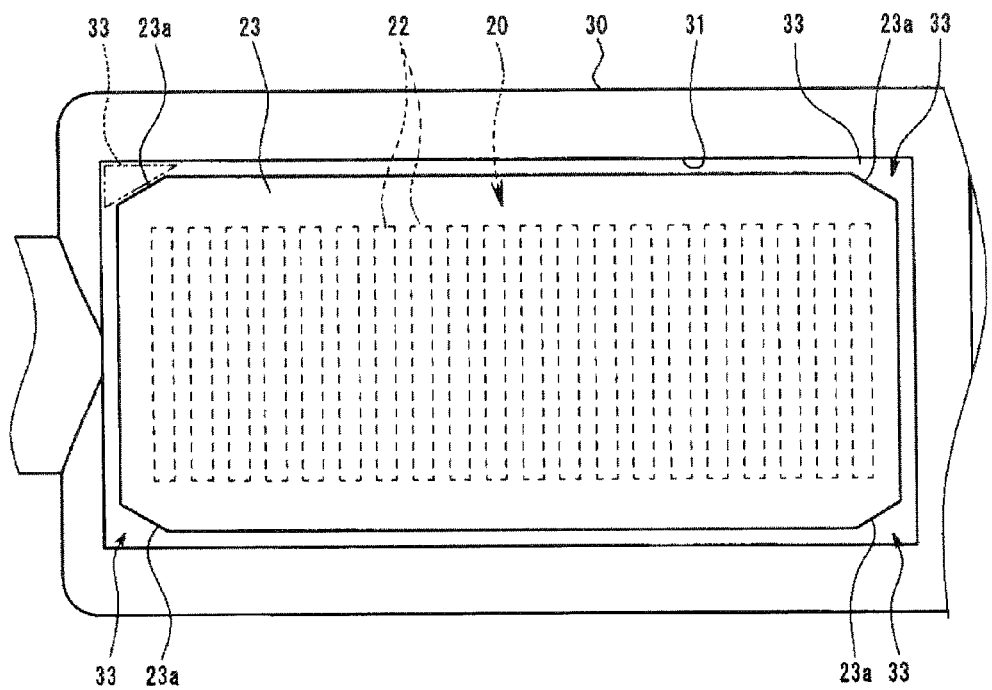
FIG. 8 is an enlarged view of the upper face of the housing that houses the ultrasound transducer section and the acoustic lens.

The first opening portion 31 is a rectangular hole portion in which the acoustic lens 23 having a quadrangular prism shape is fitted with a predetermined gap therebetween. As illustrated in FIG. 8, with the acoustic lens 23 fitted in the first opening portion 31, a gap is formed between an outer peripheral face of the acoustic lens 23 and an inner peripheral face of the first opening portion 31.

In particular, since the chamfered portions 23a are formed in the acoustic lens 23, between each of these chamfered portions 23a and a corresponding corner portion of the first opening portion 31, an adhesive outlet port 34, which is a gap having a right triangular shape, is formed. A shape of the adhesive outlet port 34 is a right triangular shape elongated in the direction in which the transducer elements 22 are aligned, as viewed in the direction facing the upper face 20a.

An adhesive 33 is charged in a gap between the outer peripheral face of the acoustic lens 23 and the inner peripheral face of the first opening portion 31, the gap including the adhesive outlet ports 34.

The second opening portion 32 is a through hole that brings the first opening portion 31 and the outside of the housing 30 into communication with each other, and the cable 21, which is a bundle of a plurality of coaxial wires, is inserted with a predetermined gap therebetween.

In the present embodiment, the total cross-sectional area of the gap between the outer peripheral face of the acoustic lens 23 and the inner peripheral face of the first opening portion 31 is larger than the total cross-sectional area of the gap between the second opening portion 32 and the cable 21. Thus, the adhesive 33 charged in the housing 30 before curing easily flows out from the gap around the first opening portion 31 and is less likely to flow out from the second opening portion 32 side. Therefore, an amount of the adhesive 33 flowing out along the cable 21 from the second opening portion 32 can be suppressed, enabling bending of the cable 21 to be prevented from being hindered by the adhesive 33 after curing.

Next, a procedure for securing the ultrasound unit 40 to the inside of the housing 30 using the adhesive 33 will be described.

Figure 9:
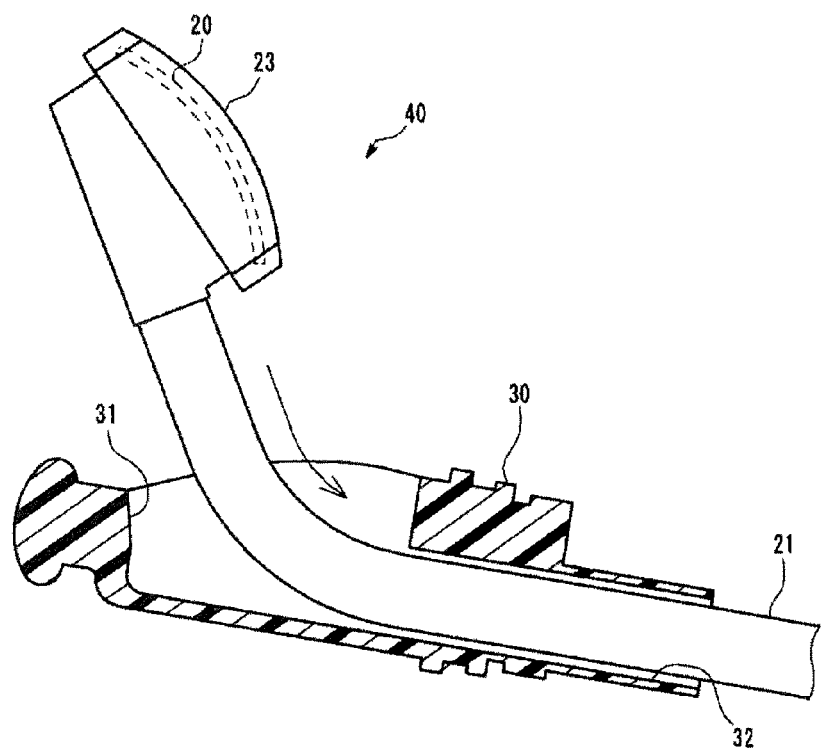
FIG. 9 is a diagram illustrating a procedure for housing the ultrasound transducer section and the acoustic lens in the housing.
Figure 10:
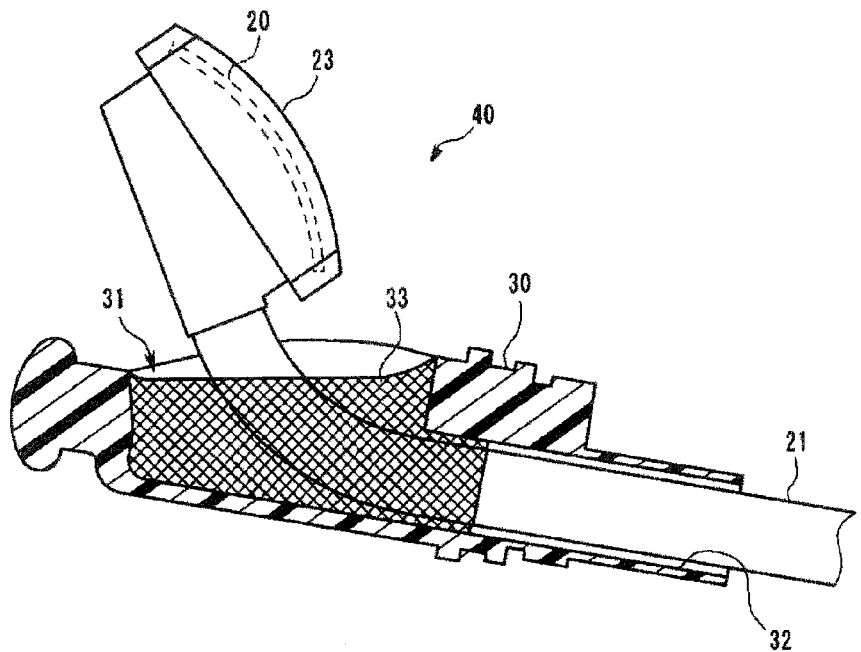
FIG. 10 is a diagram illustrating the procedure for housing the ultrasound transducer section and the acoustic lens in the housing.
Figure 11:
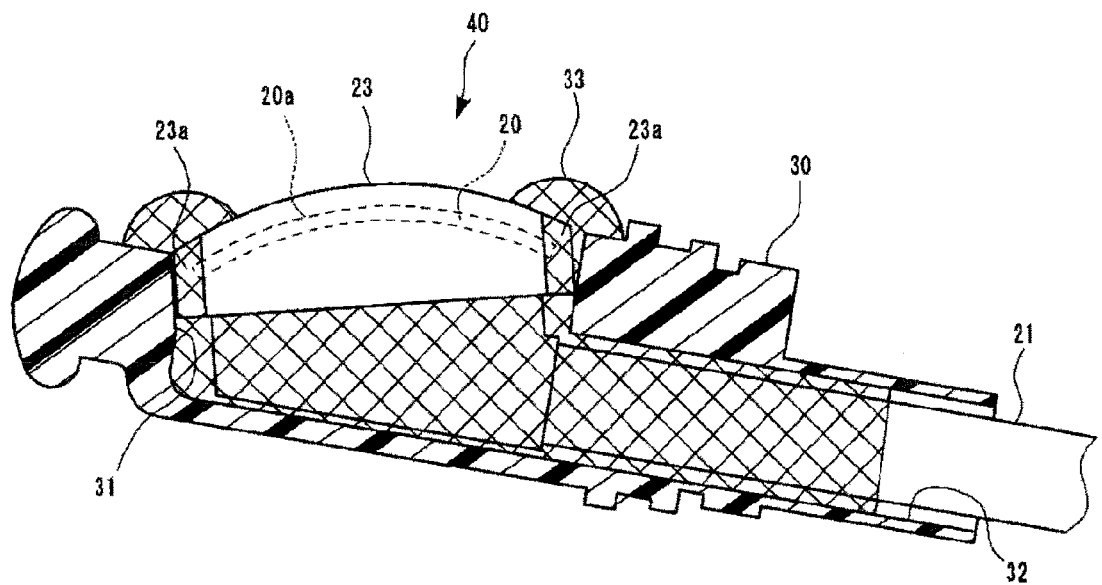
FIG. 11 is a diagram illustrating the procedure for housing the ultrasound transducer section and the acoustic lens in the housing.

First, as illustrated in FIG. 9, the cable 21 is inserted to the second opening portion 32 from the first opening portion 31 side of the housing 30. Next, as illustrated in FIG. 10, the inside of the first opening portion 31 of the housing 30 is filled with an adhesive 33 that has been defoamed and uncured. In FIGS. 10 and 11, an adhesive 33 in a deformed and uncured state is indicated by cross hatching. For the adhesive 33, one having a viscosity that causes the adhesive 33 to be less likely to flow out gravitationally from the gap between the second opening portion 32 and the cable 21 is used.

Next, as illustrated in FIG. 11, the ultrasound transducer section 20 and the acoustic lens 23 are inserted to the first opening portion 31 filled with the adhesive 33. As described above, the cross-sectional area of the gap formed in the first opening portion 31 is larger than the cross-sectional area formed in the second opening portion 32, and thus, the adhesive 33 flows out mainly from the gap formed in the first opening portion 31.

Here, since the adhesive 33 flows out from the gap formed around the entire outer peripheral face of the acoustic lens 23, the gap between the outer peripheral face of the acoustic lens 23 and the inner peripheral face of the first opening portion 31 is filled with the adhesive 33 and no air bubbles remain.

Also, after the first opening portion 31 is filled by the adhesive 33, the ultrasound transducer section 20 and the acoustic lens 23 are inserted to the inside of the first opening portion 31 so as to push the adhesive 33 out, whereby the air bubbles in the housing 30 are discharged to the outside of the housing 30 together with the adhesive 33.

In the present embodiment, the adhesive outlet ports 34 in which the gap is widened are formed, and thus, air bubbles are easily discharged together with the adhesive 33 without the air bubbles being stuck. Also, in parts of the adhesive 33 that are flowing out, a flow toward the adhesive outlet port 34 occurs, whereby air bubbles caught between the respective lower faces of the acoustic lens 23 and the ultrasound transducer section 20 and the adhesive 33 are also discharged to the outside of the housing 30 from the adhesive outlet ports 34, together with the adhesive 33.

Also, in the present embodiment, an adhesive outlet port 34 is formed at each of the four corners of the first opening portion 31 having a rectangular shape, enabling the adhesive 33 in the first opening portion 31 to flow out without ununiformity and thus enabling elimination of sites in which the adhesive 33 easily stagnates. In other words, the present embodiment enables elimination of sites inside the housing 30 in which air bubbles easily remain.

Then, after the parts of the adhesive 33 which have flowed out are wiped off, the adhesive 33 is cured, whereby the ultrasound unit 40 is secured to the inside of the housing 30.

As described above, in the ultrasound endoscope 1 according to the present embodiment, the adhesive outlet ports 34 for letting the adhesive 33 flow out are formed between the first opening portion 31 of the housing 30 and the acoustic lens 23. The formation of the adhesive outlet port 34 enables air bubbles to be prevented from remaining in the housing 30 after curing of the adhesive 33.

Here, since the adhesive outlet ports 34 are formed by providing the chamfered portions 23a at the corner portions of the acoustic lens 23, the adhesive outlet ports 34 can be provided without increasing the area of the opening of the first opening portion 31. Therefore, the present embodiment facilitates discharge of air bubbles in the adhesive 33 charged in the housing 30 without increase in dimensions of the housing 30, enabling air bubbles to be prevented from remaining In particular, in the present embodiment, each of the adhesive outlet ports 34 is formed in a right triangular shape elongated in the direction in which the transducer elements 22 are aligned, whereby the existence of adhesive outlet ports 34 is prevented from interfering with the dimensions of the transducer elements 22. Therefore, the present embodiment enables provision of the adhesive outlet ports 34 without increase in dimensions of the housing 30 and decrease in dimensions of the transducer element 22.

As described above, the present invention provides an ultrasound endoscope 1 that prevents air bubbles from remaining in a housing 30 that houses an ultrasound transducer section 20 and an acoustic lens 23, with an adhesive 33 charged therein, without increase in size of the housing 30.

The present invention is not limited to the above-described embodiment, and can be changed as appropriate without departing the spirit or idea of the invention that can be read from the claims and the entire description, and an ultrasound endoscope involving such change also falls within the technical scope of the present invention.

What is claimed is:

1. An ultrasound endoscope comprising:
an ultrasound transducer that transmits/receives ultrasound;
a housing in which the ultrasound transducer is fixed via an adhesive, and which houses the ultrasound transducer;
an inner peripheral face forming a rectangular first opening portion for exposing the ultrasound transducer, the first opening portion being formed in the housing;
an acoustic lens forming a part from an upper face to at least a side face of the ultrasound transducer; and
a chamfered portion provided at a side face of the acoustic lens, an adhesive outlet port for the adhesive to flow to an outside from the first opening portion being formed between the chamfered portion and the inner peripheral face.

2. The ultrasound endoscope according to claim 1, wherein the acoustic lens has a shape resulting from a corner of a rectangular shape being cut out, as viewed from the upper face.

3. The ultrasound endoscope according to claim 1, further comprising a cable including an end electrically connected to the ultrasound transducer;
wherein the housing includes a second opening portion via which the cable is drawn out from an inside of the first opening portion.

4. The ultrasound endoscope according to claim 3, wherein a cross-sectional area of a gap between the first opening portion and the acoustic lens, the gap including the adhesive outlet port, is larger than a cross-sectional area of a gap between the second opening portion and the cable.

5. The ultrasound endoscope according to claim 1, wherein
the ultrasound transducer includes a plurality of ultrasound elements aligned in a row along the upper face; and
a shape of the adhesive outlet port is a right triangular shape elongated in a direction in which the ultrasound elements are aligned.

* * * * *